United States Patent
Ashoori et al.

(10) Patent No.: US 10,580,435 B2
(45) Date of Patent: *Mar. 3, 2020

(54) SENTIMENT ANALYSIS OF MENTAL HEALTH DISORDER SYMPTOMS

(71) Applicant: International Business Machines Corporation, Armonk, NY (US)

(72) Inventors: Maryam Ashoori, White Plains, NY (US); Benjamin D. Briggs, Waterford, NY (US); Lawrence A. Clevenger, Rhinebeck, NY (US); Leigh Anne H. Clevenger, Rhinebeck, NY (US)

(73) Assignee: International Business Machines Corporation, Armonk, NY (US)

( * ) Notice: Subject to any disclaimer, the term of this patent is extended or adjusted under 35 U.S.C. 154(b) by 25 days.

This patent is subject to a terminal disclaimer.

(21) Appl. No.: 15/822,854

(22) Filed: Nov. 27, 2017

(65) Prior Publication Data

US 2018/0366144 A1   Dec. 20, 2018

Related U.S. Application Data

(63) Continuation of application No. 15/626,782, filed on Jun. 19, 2017, now Pat. No. 10,276,190.

(51) Int. Cl.
*G10L 25/66* (2013.01)
*G10L 15/02* (2006.01)
(Continued)

(52) U.S. Cl.
CPC .............. *G10L 25/66* (2013.01); *G06N 20/00* (2019.01); *G10L 15/02* (2013.01);
(Continued)

(58) Field of Classification Search
None
See application file for complete search history.

(56) References Cited

U.S. PATENT DOCUMENTS

| | | | |
|---|---|---|---|
| 6,185,534 B1 * | 2/2001 | Breese | G10L 17/26 704/270 |
| 7,912,720 B1 | 3/2011 | Hakkani-Tur et al. | |

(Continued)

FOREIGN PATENT DOCUMENTS

| | | |
|---|---|---|
| EP | 2229228 B1 | 7/2014 |
| WO | WO2015168606 A1 | 11/2015 |
| WO | WO2016028495 A1 | 2/2016 |

OTHER PUBLICATIONS

"Bipolar Disorder Health Center", http://www.webmd.com/bipolar-disorder/, printed Jun. 16, 2017, pp. 1-5.

(Continued)

*Primary Examiner* — Fariba Sirjani
(74) *Attorney, Agent, or Firm* — Scully, Scott, Murphy & Presser, P.C.; Kevin M. Jordan, Esq.

(57) ABSTRACT

Monitoring and analysis of a user's speech to detect symptoms of a mental health disorder by continuously monitoring a user's speech in real-time to generate audio data based, transcribing the audio data to text and analyzing the text of the audio data to determine a sentiment of the audio data is disclosed. A trained machine learning model may be applied to correlate the text and the determined sentiment to clinical information associated with symptoms of a mental health disorder to determine whether the symptoms are a symptom event. The initial determination may be transmitted to a second device to determine (and/or verify) whether or not the symptom event was falsely recognized. The trained machine learning model may be updated based on a response from the second device.

9 Claims, 4 Drawing Sheets

(51) Int. Cl.
*G10L 15/18* (2013.01)
*G16H 50/20* (2018.01)
*G06N 20/00* (2019.01)
*G10L 15/06* (2013.01)

(52) U.S. Cl.
CPC ......... *G10L 15/1815* (2013.01); *G16H 50/20* (2018.01); *G10L 15/063* (2013.01); *G10L 2015/0635* (2013.01)

(56) References Cited

U.S. PATENT DOCUMENTS

| | | | |
|---|---|---|---|
| 7,995,717 | B2 | 8/2011 | Conway et al. |
| 8,209,182 | B2 | 6/2012 | Narayanan |
| 9,959,549 | B2 | 5/2018 | Kodra et al. |
| 2010/0036660 | A1 | 2/2010 | Bennett |
| 2013/0018837 | A1* | 1/2013 | Lee ................... A61B 5/165 706/52 |
| 2014/0046660 | A1 | 2/2014 | Kamdar |
| 2014/0357668 | A1 | 12/2014 | Roseman et al. |
| 2014/0377727 | A1* | 12/2014 | Yom-Tov ............ G06F 16/951 434/236 |
| 2015/0318002 | A1* | 11/2015 | Karam ................. A61B 5/7264 704/231 |
| 2015/0373236 | A1 | 12/2015 | Thorn et al. |
| 2016/0219677 | A1 | 7/2016 | Factor et al. |
| 2018/0122371 | A1 | 5/2018 | Vangala et al. |
| 2018/0137432 | A1 | 5/2018 | Chen et al. |

OTHER PUBLICATIONS

"CQAIMH Center for Quality assessment and improvement in mental health", http://www.cqaimh.org/tool_bipolar.html, printed Jun. 16, 2017, pp. 1-2.
"Stable Resource Toolkit, The Mood Disorder Questionnaire (MDQ)—Overview", http://www.cqaimh.org/pdf/tool_mdq.pdf, printed Jun. 16, 2017, pp. 1-2.
"Stable Resource Toolkit, Bipolar Disorder Symptoms & Functioning Monitoring Form", http://www.cqaimh.org/pdf/tool_monitoringform.pdf, printed Jun. 16, 2017, 1 page.
Arbor, A., "Listening to bipolar disorder: Smartphone app detects mood swings via voice analysis", http://www.uofmhealth.org/news/archive/201405/listening-bipolar, May 8, 2014, pp. 1-5.
"Elevate the Human Experiance", http://www.cogitocorp.com/, printed Jun. 16, 2016, pp. 1-5.
Meinhold, B., "Wearable Technology" http://www.ecouterre.com/wear-a-directional-microphone-necklace-that-improves-hearing/, Feb. 14, 2014, 1 page.
https://cdn.psfk.com/wp-content/uploads/2015/06/Instamic_4192303.jpg, printed Jun. 16, 2017, 1 page.
https://www.youtube.com/watch?v=TrImAwZc2qI, Jun. 16, 2016, 4 pages of sample screenshots from video.
"Speaker recognition", https://en.wikipedia.org/wiki/Speaker_recognition, printed Jun. 16, 2017, pp. 1-6.
"Alexa Voice Service, Bring Alexa to your connected products with Amazon's intelligent cloud-based voice service", https://developer.amazon.com/alexa-voice-service, printed Jun. 16, 2017, pp. 1-14.
https://chrome.google.com/webstore/detail/voicenote-ii-speech-to-te/hfknjgplnkgjihghcidajejfmldhibfm?hl=en, printed Jun. 16, 2016, pp. 1-8.
"Rapid Cycling and its Treatment", http://www.dbsalliance.org/site/PageServer?pagename=education_brochures_bipolar_disorder_rapid_cycling, printed Jun. 16, 2017, pp. 1-4.
"Real-Time Emotional Intelligence" Cogito brochure, printed on Jun. 19, 2017, pp. 1-2.
Garcia, A., "How Language flows when movements don't: An automated analysis of spontaneous discourse in Parkinson's disease", Jun. 2016, pp. 19-28.
Bedi, G. et al., "Automated analysis of free speech predicts psychosis onset in high-risk youths", Aug. 25, 2016, pp. 1-7.
List of IBM Patents or Patent Applications Treated as Related.
Office Action dated Oct. 5, 2018, received in a related U.S. Appl. No. 15/626,782.
Office Action dated Apr. 3, 2018 received in parent U.S. Appl. No. 15/626,782, 46 pages.
Notice of Allowance dated Dec. 19, 2018, received in a related U.S. Appl. No. 15/626,782.

\* cited by examiner

SENTIMENT ANALYSIS OF MENTAL HEALTH DISORDER SYMPTOMS

BACKGROUND

The present disclosure relates to the analysis of mental of mental health disorder symptoms using sentiment analysis.

Mental health disorders including, for example, bi-polar disorder, may begin during early childhood and may continue into adulthood. Bi-polar disorder, for example, may be characterized by intense mood swings that include emotional highs (e.g. euphoric feelings) and lows (e.g., depression). The mood shifts may occur only a few times a year or as often as several times a week. The Child and Adolescent Bipolar Foundation estimates that at least three quarters of a million American children and teens may suffer from bipolar disorder, although many are not diagnosed. According to the National Institute of Mental Health, in a given year, bipolar disorder affects about 5.7 million American adults, or about 2.6% of the U.S. population 18 and older.

According to Center for Quality Assessment and Improvement in Mental Health, bipolar disorder is frequently unrecognized, under diagnosed, and inappropriately treated. For example, patients generally do not recognize or spontaneously report the symptoms of mania, e.g., a mental illness marked by periods of great excitement, euphoria, delusions, and overactivity, and hypomania, e.g., a mild form of mania, marked by elation and hyperactivity, as they view these periods as normal happiness or well-being.

Forms, such as, for example, the Mood Disorder Questionnaire (MDQ) and the Bipolar Disorder Symptoms & Functioning Monitoring Form, both published by the center for quality assessment and improvement in mental health (CQAIMH), have been designed to aid clinicians in the screening of present and past episodes of mania and hypomania. However the accuracy of the data found in these forms may be questionable because the forms may be incorrectly filled out.

BRIEF SUMMARY

One aspect of the present disclosure is a computer-implemented method, which includes monitoring speech by an audio input device, generating audio data by the audio input device based on monitored speech, transcribing the audio data to text, analyzing the text of the audio data by a computing device to determine a sentiment, correlating the text and determined sentiment to clinical information associated with one or more symptoms of a health disorder, and determining whether or not the symptoms are a symptom event.

Other embodiments of the present invention include systems, and computer program products.

BRIEF DESCRIPTION OF THE DRAWINGS

The details of the present disclosure, both as to its structure and operation, can best be understood by referring to the accompanying drawings, in which like reference numbers and designations refer to like elements and wherein.

DETAILED DESCRIPTION

In aspects of the present disclosure, the mental health of a patient may be detected, monitored, and analyzed by continuously gathering data about the patient during their everyday life. The data may be analyzed to determine whether the patient may be exhibiting symptoms of a mental disorder, for example, mood changes in a patient may be symptoms of bi-polar disorder. If the data indicates that the patient may be exhibiting symptoms of a disorder, the patient or a clinician may be notified so that services may be provided and the data may be stored in a database for later use.

Figure 1:
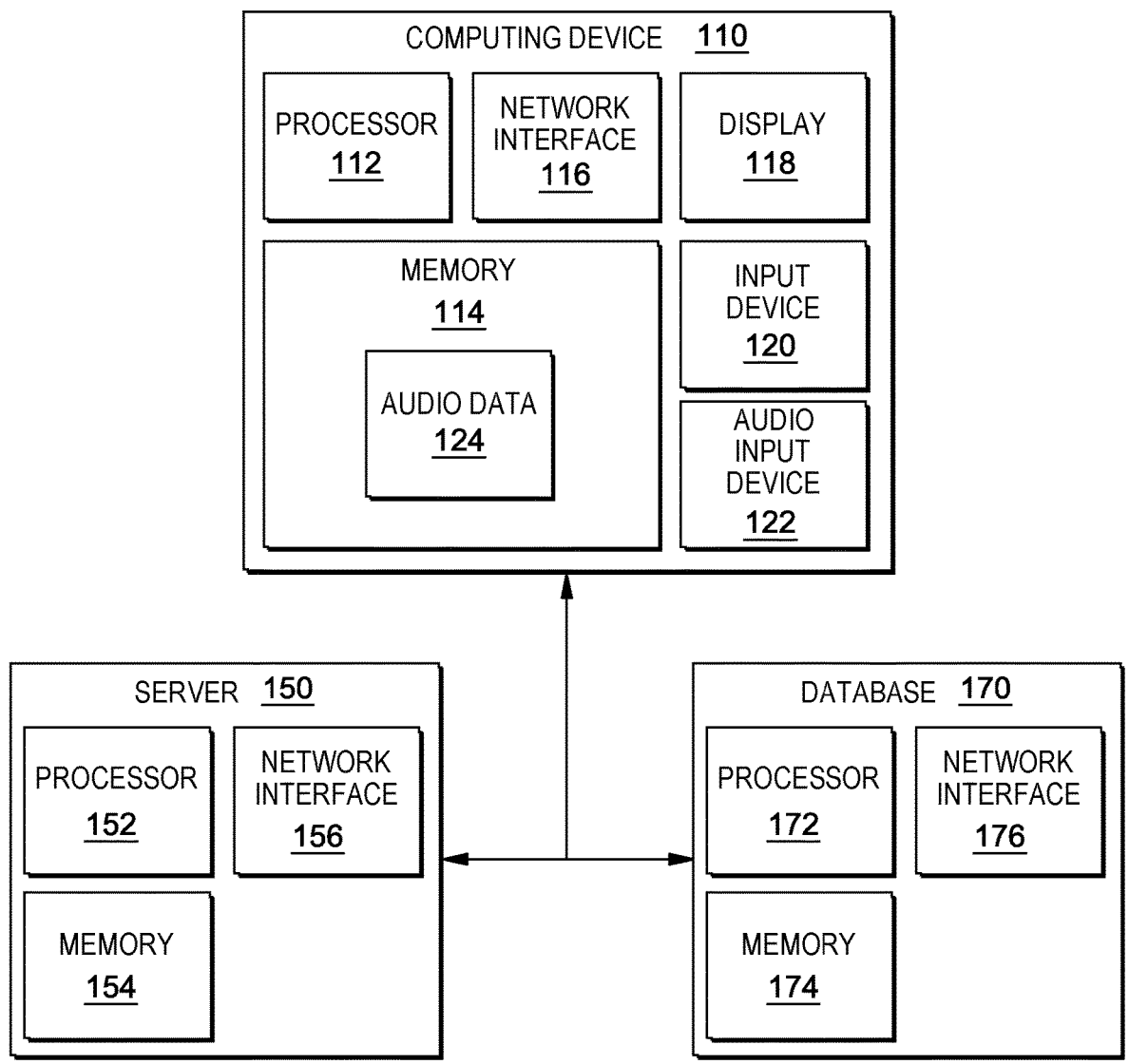
FIG. 1 illustrates an exemplary system in accordance with the present disclosure.

FIG. 1 illustrates an exemplary system in accordance with the present disclosure. As depicted, a system 100 for monitoring a user, e.g., a patient, for symptoms of a mental disorder includes a computing device 110, a server 150, and a database 170.

Computing device 110 includes at least one processor 112, memory 114, at least one network interface 116, a display 118, an input device 120, an audio input device 122 and may include any other features commonly found in a computing device. In some aspects, computing device 110 may be embodied as a, a personal computer, laptop, tablet, smart device, smart phone, smart watch, smart wearable device, or any other similar computing device that may be used by a user or a clinician. In some aspects, for example, computing device 110 may include program modules (not depicted) configured to gather or receive data from the user and may transmit the gathered or received data to server 150 for further processing and analysis (via other program modules (also not depicted) to determine whether the data indicates that the user may have a mental disorder. In some aspects, computing device 110 or another computing device (not depicted) may also be configured to receive data from server 150 regarding an analysis result of a user. For example, such computing device(s) may be monitored by a user-authorized third party, such as a user-authorized clinician.

In some aspects, some or all of the processing and analysis may be performed directly on computing device 110. In some aspects, for example, computing device 110 may execute or implement an application that performs monitoring of the user's mental health.

Processor 112 may include, for example, a microcontroller, Field Programmable Gate Array (FPGAs), or any other processor that is configured to perform various operations. Processor 112 may be configured to execute instructions as described below. These instructions may be stored, for example, in memory 114. In some aspects, for example, memory 114 may store instructions to implement a mental health monitoring application that implements any of the functionality described below.

Memory 114 may include, for example, non-transitory computer readable media in the form of volatile memory, such as random access memory (RAM) and/or cache memory or others. Memory 114 may include, for example, other removable/non-removable, volatile/non-volatile storage media. By way of non-limiting examples only, memory 114 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Network interface 116 is configured to transmit and receive data or information to and from a server 150 or any other computing device via wired or wireless connections. For example, network interface 116 may utilize wireless technologies and communication protocols such as Bluetooth®, WIIFI (e.g., 802.11a/b/g/n), cellular networks (e.g., CDMA, GSM, M2M, and 3G/4G/4G LTE), near-field communications systems, satellite communications, via a local area network (LAN), via a wide area network (WAN), or any other form of communication that allows computing device 110 to transmit or receive information to or from server 150 or database 170.

Display 118 may include any display device that is configured to display information to a user of computing device 110. For example, in some aspects, display 118 may include a computer monitor, television, smart television, or other similar displays. In some aspects, display 118 may be integrated into or associated with computing device 110, for example, as a display of a laptop, smart phone, smart watch, or other smart wearable devices, as a virtual reality headset associated with computing device 110, or any other mechanism for displaying information to a user. In some aspects, display 118 may include, for example, a liquid crystal display (LCD), an e-paper/e-ink display, an organic LED (OLED) display, or other similar display technologies. In some aspects, display 118 may be touch-sensitive and may also function as an input device 120.

Input device 120 may include, for example, a keyboard, a mouse, a touch-sensitive display 118, a keypad, a microphone, or other similar input devices or any other input devices that may be used alone or together to provide a user with the capability to interact with computing device 110.

Audio input device 122 may include, for example, a microphone or other similar device that is configured to sense or gather audio information, e.g., speech, statements, or other verbal noises, made by the user and the sensed or gathered audio information may be stored as audio data 124 in memory 114. Non-limiting examples of audio input devices 122 may include wearable directional microphones, wearable audio recorders, microphone necklaces, cell phone microphone, wireless earpieces, or other similar devices. In some aspects, audio input device 122 may be a directional microphone oriented toward the user so as to capture the user's speech and other sounds while filtering out background environmental sounds.

In some aspects, speaker recognition technologies may be implemented by computing device 110 to differentiate between sounds received from the user and sounds received from other sources. For example, the audio information captured by audio input device 122 may be filtered using the speaker recognition technologies and the resultant output may be stored as audio data 124 in memory 114. For example, in some aspects, audio data 124 may include only those sounds determined to be received from the user by the speaker recognition technologies. A few (non-limiting) examples of speaker recognition technologies include: Alexa Voice Services™ (AVS), Watson SST™, Voice Note™, and other similar voice recognition technologies.

In some aspects, the audio data 124 may include any captured sound, including those sources from the user or from other sources, and the speaker recognition technologies may be applied by server 150 to the audio data 124 to differentiate between the sounds made by the user and sounds made by other sources.

In some aspects, audio input device 122 may be a separate device from computing device 110 and may communicate or transmit audio data 124 to computing device 110 for storage in memory 114. In some aspects, for example, audio input device 122 may communicate with computing device 110 via network interface 116 using any of the above described communication protocols or any other similar communication protocol.

Server 150 includes a processor 152, memory 154, and a network interface 156 that may include similar functionality as processor 112, memory 114, and network interface 116. In some aspects, server 150 may, for example, be any computing device, server, or similar system that is configured to interact with or provide data to computing device 110. In some aspects, for example, server 150 may include one or more servers that are configured to perform cognitive analysis of the audio data 124 gathered by audio input device 122 of computing device 110. For example, server 150 may receive audio data 124 from computing device 110 and may analyze the audio data 124 to determine whether any symptoms of mental health disorders are present in the audio data 124.

In some aspects, for example, server 150 may be configured to analyze both structured and unstructured data by applying advanced natural language processing, information retrieval, knowledge representation, automatic cognitive reasoning, and machine learning technologies. An example system that may be used by server 150 to analyze audio data 124 gathered from a user's speech includes IBM Watson®, a product of International Business Machines Corporation of Armonk, N.Y. In some aspects, for example, server 150 may be configured to analyze a sentiment of the audio data 124 and the duration that the sentiment lasts to determine when mood swings happen, how quickly, and for how long.

Database 170 may store the results of the analysis performed by server 150.

Figure 2:
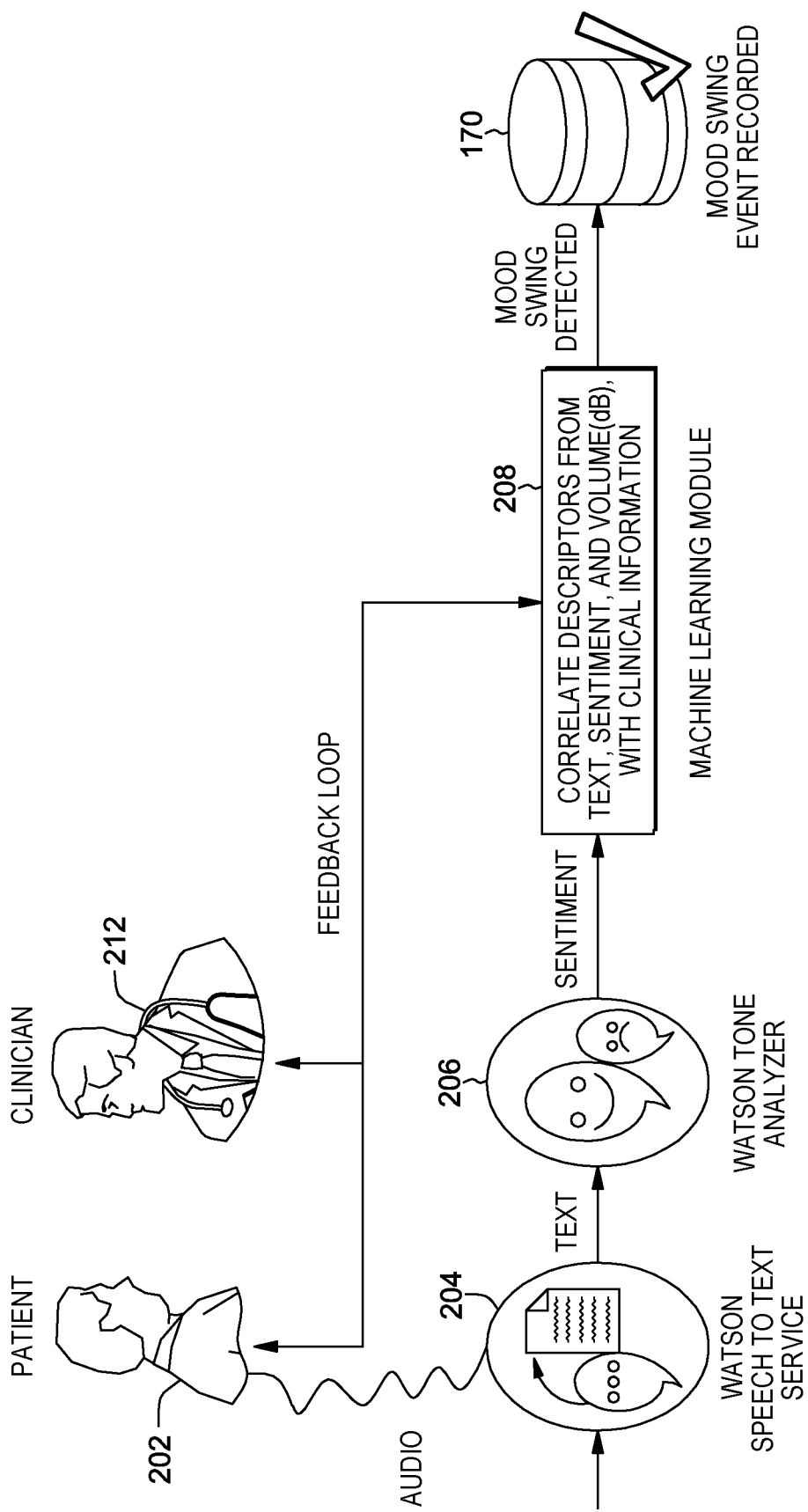
FIG. 2 illustrates another exemplary system in accordance with the present invention.

FIG. 2 illustrates another exemplary system in accordance with the present disclosure. With reference now to FIG. 2, the speech or other audible sounds made by a patient 202 may be continuously monitored by computing device 110. For example, audio input device 122 may monitor the patient 202's speech and generate a continuous stream of audio data 124. The audio data 124 may be temporarily or semi-permanently stored in memory 114 and may be transmitted to server 150, e.g., via network interfaces 116 and 156.

In some aspects, server 150 may transcribe the audio data 124 to text using known transcription technology 204. One (non-limiting) example of such transcription technology, is the IBM Watson Speech To Text Service™.

In some aspects, server 150 may analyze 206 the transcribed text of the patient's speech to determine one or more attributes of the patient's speech. One (non-limiting) example of such analysis technology 206 is the IBM Watson Tone Analyzer™. In some embodiments, server 150 may determine a tone or sentiment of the patient's speech. For example, server 150 may be configured to determine, e.g., whether the patient is happy, angry, sad, or other moods/sentiment based on the determined speech attributes.

In some aspects, by way of further example, the analysis of the patient's speech by server 150 may include monitoring the patient's speech attributes in real-time by evaluating a rate of the patient's speech in the audio data 124. For example, server 150 may determine a patient's mood or behavior, based on an analysis of the audio data 124. For example, it may be detected that the patient is in a depressed state when the patient's rate of speech is low, e.g., below a predetermined or patient specific low threshold, and that the patient is in a manic state when the patient's rate of speech is high, e.g., above a predetermined or patient specific high threshold. In some aspects, for example, a baseline rate of speech may be determined for the patient based on historical audio data of the patient and the high and low thresholds may be determined based on the historical audio data.

In some aspects, for example, the determined speech attributes, e.g., tone or sentiment, rate of speech, volume level (dB), or any changes in the patient's speech attributes as compared to historically established baseline behaviors of the patient, may be input into a machine learning module 208 which is trained to correlate descriptors from the converted text of the patient's speech, determined sentiment of the patient's speech, and volume level (dB) of the patient's speech with clinical information, e.g., information on symptoms and corresponding mental health diagnoses, using algorithms such as, for example, multiple linear regression, partial least squares fit, support vector machines, and random forest. In some aspects, for example, machine learning module 208 may be configured to analyze the past pattern of a patient's mood swings to predict future behaviors. For example, the machine learning module 208 may be trained using supervised learning where the training inputs and testing feature vectors may have the same elements. The training values may be measured during a baseline session held with a patient for training purposes and the testing values may be generated during real-time monitoring of the patient.

In some aspects, the feature vector may be represented as a list of real numbers or integers including, but not limited to rate of speech (Hz), volume of speech (dB), repeating speech patterns (number of repeated words per time interval), sentiment (e.g., anger=1, joy=2, sadness=3, etc.), mental health diagnosis (e.g., no diagnosis=1, mild diagnosis=2, severe diagnosis=3, etc.), physical manifestations of symptoms (e.g., arm waving=1, pacing=2, etc.), medication (Lamictal=1, Seroquel=2, Abilify=3, Klonopin=4, etc.), treatments (behavior modification=1, music therapy=2, group therapy=3, etc.), or other similar feature vector elements.

In some aspects, the output of the selected classifier may be evaluated in terms of the false acceptance rate vs. the false rejection rate, also known as the equal error rate (EER). This accuracy percentage may determine the confidence level that the patient is exhibiting signs of bipolar or other mental health disorder behavior at any point in time. In some aspects, the threshold may be determined on an individual basis for each patient. In some aspects, until a baseline behavior for a patient is established, the threshold may be determined based on historic data from patients with a similar behavioral profile. For example, a mood swing can last for hours, days, or months, depending on the individual patient.

Machine learning algorithms may also be used to determine which features have the most influence on the result. This information, combined with patterns determined from tracking the machine learning accuracy results may be used to predict future behavior. For example, if rapid speech has been shown through machine learning to indicate a change toward bipolar behavior for an individual, this behavior may be monitored as a high priority for that patient.

In some aspects, the analyzed frequency and patterns of mood swings found in the audio data 124 may be used to evaluate the effectiveness of medications or treatments. For example, the outcome of the analysis of the audio data 124 may be compared to the analysis of historical audio data, e.g., the baseline for the patient, to determine whether a medication or treatment is effective in reducing the patient's symptoms.

In some aspects, the output result of machine learning module 208, e.g., a determination that a mood swing has occurred for the patient, may be stored or recorded in database 170, for later use. In some aspects, the output result of machine learning module 208 may be transmitted to a computing device 110 of patient 202, a computing device 110 of a clinician 212, and/or both, for further analysis. In some aspects, for example, the computing device 110 of a clinician 212 may receive an output result from the machine learning module 208, e.g., from server 150, that indicates that the patient is exhibiting symptoms of a mental health disorder. The computing device 110 may alert the clinician 212 of the results and in some aspects, may propose scheduling a checkup or counseling session with the patient 202 to the clinician 212 to discuss the symptoms.

Figure 3:
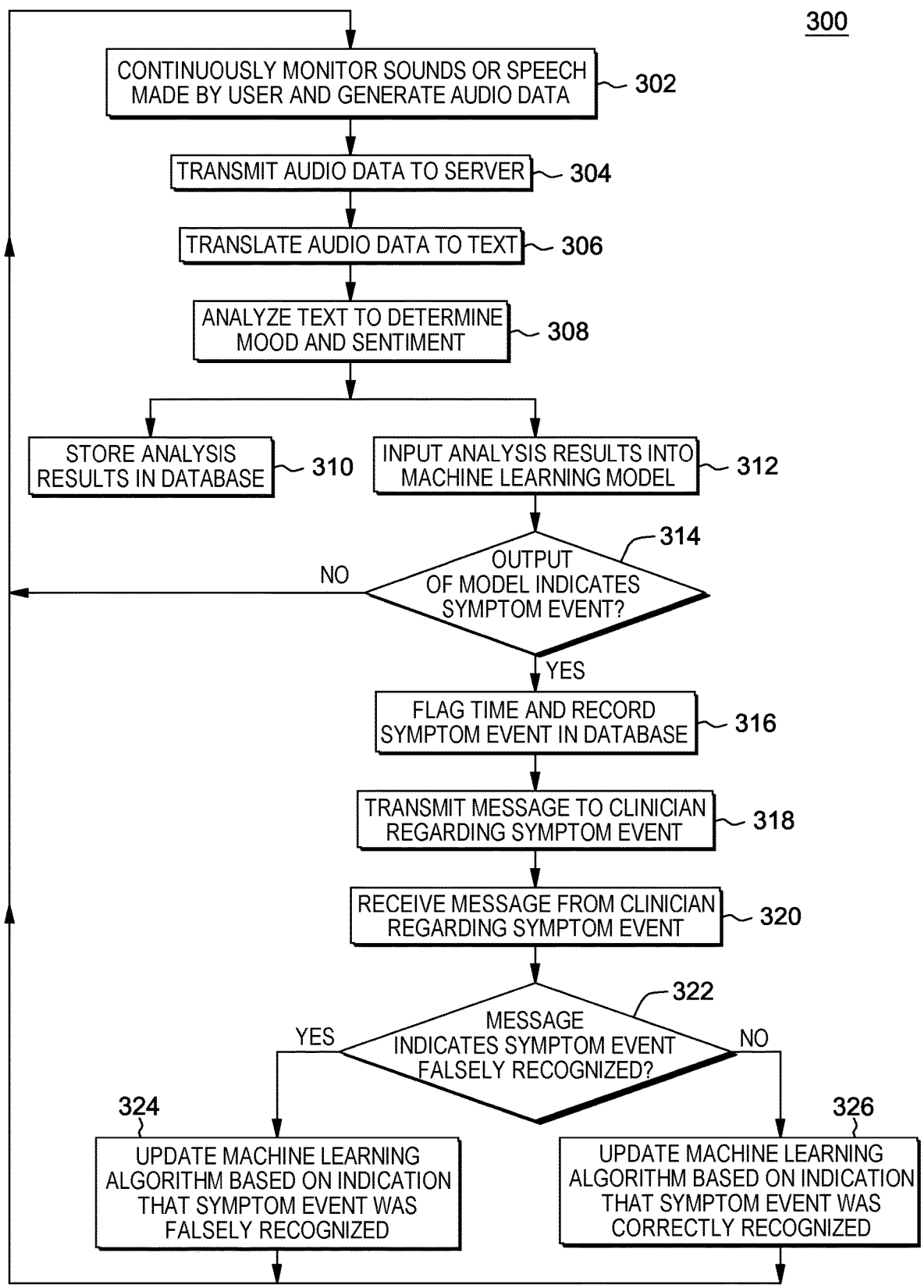
FIG. 3 illustrates an exemplary method in accordance with the present invention.

FIG. 3 illustrates an exemplary method in accordance with the present disclosure. With particular reference now to the example depicted in FIG. 3, exemplary method 300 continuously monitors a user, e.g., a patient, for symptoms of a mental health disorder.

At 302, audio input device 122 continuously monitors any sounds or speech made by the user and generates audio data 124. In some aspects, audio input device 122 may transmit the audio data 124 to the computing device 110 of the user for storage in memory 114. In some aspects, audio input device 122 may be included as a component of computing device 110 and may store the audio data 124 in memory 114 directly. The audio data 124 may be stored temporarily in memory 114, e.g., in a buffer, or may be stored semi-permanently in memory.

At 304, the computing device 110 of the user transmits the audio data 124 to server 150. In some aspects, the computing device 110 of the user may continuously stream the audio data 124 to the server 150 in real-time. In some aspects, some or all of the method may be performed by computing device 110

At 306, the server 150 transcribes the received audio data 124 to text using a speech to text engine, e.g., using the IBM Watson Speech To Text Service™.

At 308, server 150 analyzes the text of the audio data 124 to determine a mood or sentiment of the user's speech, e.g., using a sentiment analysis tool such as the IBM Watson Tone Analyzer™.

In some aspects, for example, server 150 may analyze the text to determine a mood of the patient's speech, analyze the text or audio data 124 to determine a rate of the user's speech, or may determine any other speech characteristics of the user's speech that may be used to determine whether the user is exhibiting symptoms of a mental health disorder.

In some aspects, the audio data 124 may also be analyzed, for example, to determine changes in the volume level (dB) of the user's speech, or other similar non-textual components of the user's speech.

At 310, the results of the analysis and in some aspects the audio data 124 are transmitted to database 170 for storage. For example, as real-time audio data 124 continues to accumulate, database 170 may continue to store the audio data 124 and corresponding analysis results for later use as historical data for the user or for other users. For example, the audio data 124 and corresponding analysis results stored in database 170, e.g., historical data, may be later used to develop a behavioral baseline for the user that may be compared to the real-time audio data 124 to make determinations on whether the user is exhibiting any new or different symptoms, to determine the effectiveness of drugs or other treatments, or other similar uses. In some aspects, the historical data stored in database 170 may be used as a training corpus for training a machine learning model 208 (FIG. 2) to assess users for symptoms of mental health disorders. In some aspects, a plurality of users may have their audio data 124 and corresponding analysis results stored in database 170 and the audio data 124 and corresponding analysis results for all of the users may be used as inputs for training machine learning model 208 to detect symptoms of mental health disorders.

At 312 machine learning module 208 (FIG. 2) receives the results of the analysis of the audio data 124 generated in real-time from the user, e.g., the tone, sentiment, mood, rate, etc., and generates an output indicating whether or not a mood swing or other symptom has been detected at 314. If no mood swing has been detected, the method returns to 302 and continues to monitor the speech or sounds made by the user and generating audio data.

At 316, if a mood swing or other symptom has been detected, the time of the mood swing or other symptom may be flagged, e.g., a timestamp may be generated based on a current time or a start time of the mood swing in the audio data 124 may be flagged, and the mood swing or other symptom may be recorded with the flagged time in database 170. In some embodiments, the mood swing or other symptom may be referred to as a symptom event.

At 318, server 150 may transmit a message to a computing device 110 of a clinician associated with the user in response to the detection of a mood swing or other symptom or in response to a symptom event being recorded in database 170. In some aspects, for example, the message may include a reference to the audio data 124 in database 170, the results of the analysis of the audio data, the flagged time, and the output of the machine learning module 208.

At 320, server 150 receives from the clinician, e.g., via computing device 110 of the clinician, a message indicating whether the symptom event is valid (or on the other hand, was falsely recognized). For example, the clinician may review the message and any of the audio data 124, results of the analysis, flagged time, and output of the machine learning module 208 to determine whether the symptom event is falsely recognized. For example, in some aspects, the clinician may determine that the audio data 124 does not indicate any symptoms of a mental health disorder. In some aspects, the clinician may confirm that the audio data 124 does indicate that the patient is experiencing symptoms of a mental health disorder.

At 322, server 150 determines whether the message received from the computing device 110 of the clinician indicates that the symptom event was falsely recognized or correctly recognized.

If the message indicates that the symptom event is falsely recognized, server 150 may update the machine learning module 208 in real-time based on the indication at 326. For example, server 150 may use the indication that the symptom event was falsely recognized to further train machine learning module 208 by correlating the audio data 124 and corresponding analysis results with a confirmed non-symptom event outcome. The method may then proceed to 302 and audio input device 122 may continue monitoring the user's speech and sounds and generating audio data 124.

If the message indicates that the symptom event is correctly recognized, server 150 may update the machine learning module 208 in real-time based on the indication at 326. For example, server 150 may use the indication that the symptom event was correctly recognized to further train machine learning module 208 by correlating the audio data 124 and corresponding analysis results with a confirmed symptom event outcome. The method may then proceed to 302 and audio input device 122 may continue monitoring the user's speech and sounds and generating audio data 124.

The following example scenarios using system 100 (FIG. 1) and method 300 (FIG. 3) will now be described.

In the first example scenario, a user named Judy is suffering from bi-polar disorder and receiving bi-polar medication. Judy is doing very well with her bipolar medication and enjoys spending time with other residents in a rehabilitation facility. If Judy has a manic episode, however, she may become dangerous to both herself and the other residents at the facility. Staff at the rehabilitation facility is not available to watch her at all times.

Judy has a computing device 110, e.g., a smart watch, that continuously monitors and analyzes her words when she is in the common room. For example, her location may be identified by a GPS system associated with her smart watch. The audio data 124 from Judy's smart watch may be transmitted to a server 150 for analysis as described above. If server 150 determines that a pattern in Judy's speech has changed, e.g., as a precursor to a manic episode, a message may be sent to a nurse at the rehabilitation facility providing details of the pattern change and an indication that Judy may need help. In some aspects, a message may also be sent to Judy indicating that she should remove herself from the current situation.

In a second example scenario, a user named Joe is a senior high school student going through tremendous pressure to prepare and submit college application forms. Joe has a computing device 110, e.g., a smart watch, that continuously monitors and analyzes his words. The audio data 124 from Joe's smart watch may be transmitted to a server 150 for analysis as described above. During analysis, server 150 may determine that Joe has experienced a period of extreme joy followed by an extreme sadness and that this pattern has been occurring several times a week. A message may be transmitted from server 150 to Joe's family doctor providing the doctor with the audio data 124 and the analysis results. Joe's family doctor may then invite Joe to the clinic for further testing.

Figure 4:
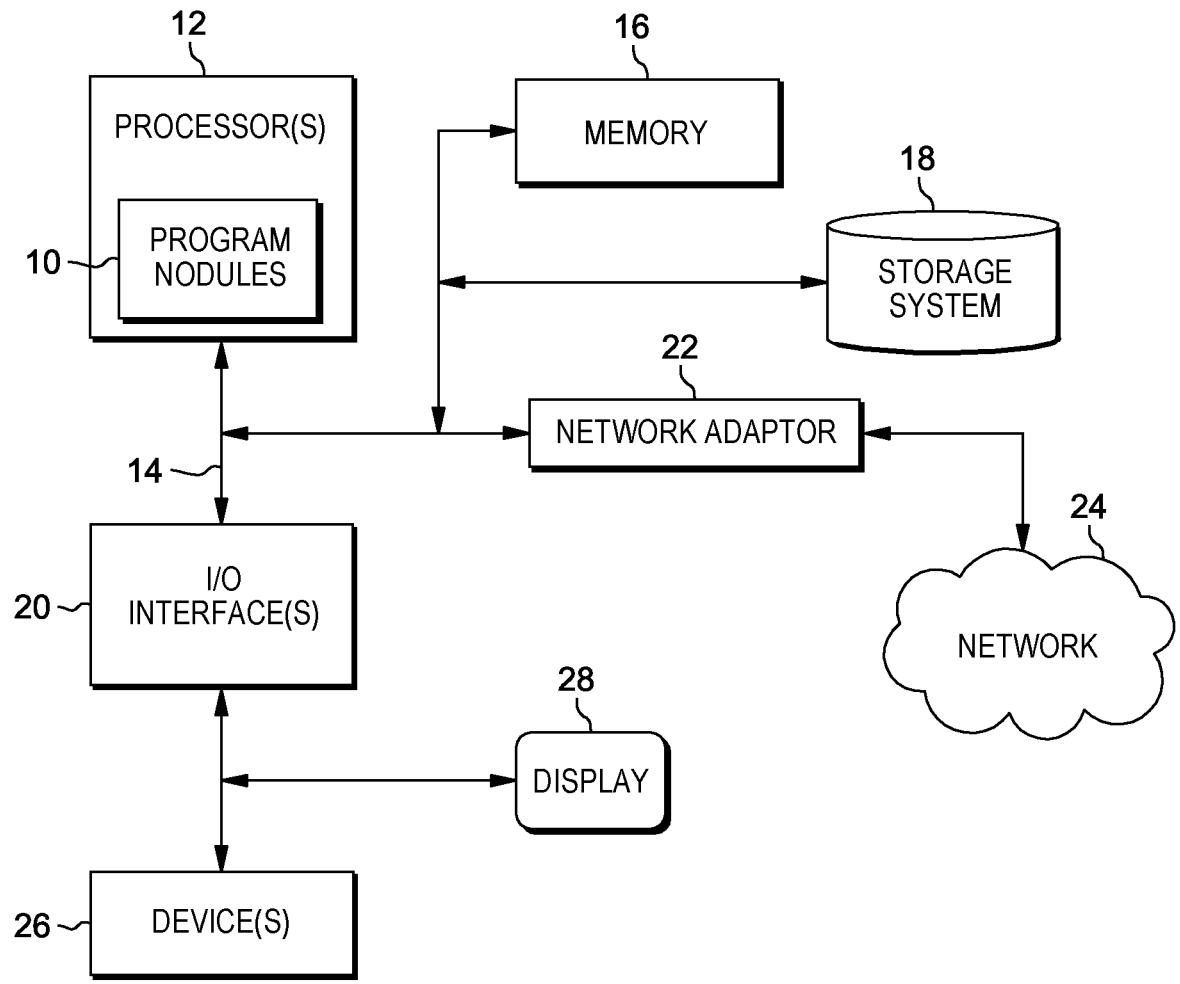
FIG. 4 illustrates yet another exemplary system in accordance with the present invention.

FIG. 4 illustrates yet another exemplary computer or processing system in accordance with the present disclosure. Some aspects may implement any portion of system 100, computing device 110, server 150, database 170, systems, methods, and computer program products described herein. A computer system is only one example of a suitable processing system and is not intended to suggest any limitation as to the scope of use or functionality of embodiments of the methodology described herein. The system shown may be operational with numerous other general purpose or special purpose computing system environments or configurations. Examples of well-known computing systems, environments, and/or configurations that may be suitable for use with the processing system may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

An exemplary computer system may be described in the general context of computer system executable instructions. With reference now to FIG. 5, the computer system executable instructions can be embodied as one or more program modules 10, being executed by processor(s) 12 of the computer system. Generally, program modules 10 may include routines, programs, objects, components, logic, data structures, and so on that perform particular tasks or implement particular abstract data types.

In some aspects, the computer system may be practiced in distributed cloud computing environments where tasks are performed by remote processing devices that are linked through a communications network ("cloud"). In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include one or more program (software) module(s) 10 that perform the methods described herein. The module 10 may be programmed into the integrated circuits of the processor 12, or loaded from memory 16, storage device 18, network 24 and/or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

Memory 16 can include computer system readable media in the form of volatile memory, such as random access memory (RAM) and/or cache memory or others (sometimes referred to "system memory"). Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present disclosure are described herein with reference to flowchart illustrations and/or block diagrams. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus (or system) to produce a machine, such that the instructions, when executed via the processor of the computer, or other programmable apparatus or system, create means for implementing the functions/acts specified in the flowchart and/or block diagram block or blocks. These computer readable program instructions may also be stored in a computer readable storage medium that can direct a computer, a programmable apparatus, system, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable apparatus, system or other device to cause a series of operational steps to be performed by the computer, other programmable apparatus, system or other device to produce a computer implemented process, such that the instructions which execute on the computer, other programmable apparatus, system, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by systems that perform the specified functions or acts.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A computer-implemented method, comprising:
monitoring continuously and in real-time, by an audio input device associated with a first party, speech from the first party;
generating, by the audio input device, audio data based on monitored speech;
transcribing, using a hardware processor of a computing device, the audio data to text;
analyzing, by the computing device, the text of the audio data to determine a sentiment;
training a model, using machine learning, to correlate the text and the determined sentiment to clinical information associated with one or more symptoms of a health disorder;
storing the audio data, the text, the determined sentiment and an output of the trained machine learning model in a database as historical data, wherein the trained machine learning model is trained based at least in part on the historical data that is stored in the database; and
developing, over time, a behavioral baseline condition for the first party based on a history of audio data and corresponding text sentiment analysis results;
comparing a result of analyzing the text of the current audio data against a baseline condition of said first party, and
determining, based on said comparison, whether the first party is exhibiting a new or different symptom; and
scheduling, via an interface device, a checkup or appointment with a health care practitioner regarding said new or different symptom,
wherein a symptom includes a mood swing event, said method further comprising:
analyzing, by the hardware processor, the sentiment of the speech and a duration of said sentiment to identify a mood swing event including a time of occurrence, how quickly the mood swing event occurs, and for how long a mood swing event occurs;
determining, by the hardware processor, over time, a pattern and frequency of each identified mood swing event;
comparing a determined pattern and frequency of the mood swing events against a database of known mood swing patterns;
predicting, based on said comparing determined frequency and pattern of mood swing events, a mood swing occurrence exhibited by said first party in the future, and
generating an output message via an interface, said message indicating said predicted potential mood swing of said first party.

2. The method of claim 1, further comprising applying the trained machine learning model to correlate the text, the determined sentiment, and at least one speech attribute of the audio data to the clinical information associated with one or more symptoms of a health disorder.

3. The method of claim 2, wherein the at least one speech attribute is selected from a group consisting of: a volume level and a rate of speech.

4. The method of claim 1, further comprising:
determining, by the hardware processor, whether or not symptoms are a symptom event, and upon determining that the symptoms are a symptom event,
determining that the symptom event was falsely recognized; and
updating the trained machine learning model based on the audio data, the text and the determined sentiment, with a confirmed non-symptom event, in response to determining that the symptom event was falsely recognized.

5. The method of claim 1, further comprising:
determining whether or not symptoms are a symptom event, and upon determining that the symptoms are a symptom event,
determining the symptom event was correctly recognized; and
updating the trained machine learning model based on the audio data, the text and the determined sentiment with a confirmed symptom event, in response to determining the symptom event was correctly recognized.

6. The method of claim 1, further comprising:
transmitting a message including an indication of whether or not the symptoms are a symptom event to a computing device associated with a second user;
receiving from the computing device associated with the second user a message indicating whether or not the symptom event was falsely recognized; and
updating the trained machine learning model based on the received message.

7. The method of claim 1, further comprising:
determine, using the hardware processor, based on said comparing a result of analyzing the text of the current audio data against the baseline condition, whether a medication or treatment administered to said first party is effective in reducing the first party's symptoms.

8. The method of claim 1, further comprising:
training, using said hardware processor, said machine learning model based at least in part on training inputs comprising a testing feature vector, said testing feature vector having data representing one or more of: a first party's rate of speech, a volume level of speech, a repeating speech pattern, a determined sentiment, a determined mental health diagnosis, an indication of a physical manifestation of said one or more symptoms, medication, and treatments applied to said first party.

9. The method of claim 1, further comprising:
transmitting, using said hardware processor, a message including an indication of a detected mood swing event associated with the first party to a second party;
receiving, from a device associated with the second party, a message indicating whether or not the mood swing event was correctly recognized or falsely recognized; and
updating the trained machine learning model based on the received message.

* * * * *